United States Patent
Maeda

(10) Patent No.: US 10,449,338 B2
(45) Date of Patent: Oct. 22, 2019

(54) CATHETER AND METHOD OF MANUFACTURING THE SAME

(71) Applicant: TERUMO KABUSHIKI KAISHA, Shibuya-ku, Tokyo (JP)

(72) Inventor: Naoyuki Maeda, Odawara (JP)

(73) Assignee: TERUMO KABUSHIKI KAISHA, Shibuya-Ku, Tokyo (JP)

(*) Notice: Subject to any disclaimer, the term of this patent is extended or adjusted under 35 U.S.C. 154(b) by 204 days.

(21) Appl. No.: 15/433,402

(22) Filed: Feb. 15, 2017

(65) Prior Publication Data
US 2017/0157373 A1 Jun. 8, 2017

Related U.S. Application Data

(63) Continuation of application No. PCT/JP2015/074625, filed on Aug. 31, 2015.

(30) Foreign Application Priority Data

Sep. 4, 2014 (JP) ................................ 2014-180092

(51) Int. Cl.
*A61M 25/10* (2013.01)
*A61M 25/01* (2006.01)
(Continued)

(52) U.S. Cl.
CPC .. *A61M 25/10184* (2013.11); *A61M 25/0102* (2013.01); *A61M 25/1029* (2013.01);
(Continued)

(58) Field of Classification Search
CPC ............ A61M 25/10; A61M 25/1006; A61M 25/1009; A61M 25/1018;
(Continued)

(56) References Cited

U.S. PATENT DOCUMENTS

| 5,647,848 A | 7/1997 | Jørgensen |
| 2005/0271844 A1 | 12/2005 | Mapes et al. |

(Continued)

FOREIGN PATENT DOCUMENTS

| JP | 2008-501408 A | 1/2008 |
| JP | 2008-253800 A | 10/2008 |

(Continued)

OTHER PUBLICATIONS

International Search Report (PCT/ISA/210) dated Nov. 24, 2015, by the Japan Patent Office as the International Searching Authority for International Application No. PCT/JP2015/074625.
Written Opinion (PCT/ISA/237) dated Nov. 24, 2015, by the Japan Patent Office as the International Searching Authority for International Application No. PCT/JP2015/074625.

*Primary Examiner* — Bhisma Mehta
*Assistant Examiner* — James D Ponton
(74) *Attorney, Agent, or Firm* — Buchanan Ingersoll & Rooney PC

(57) ABSTRACT

A catheter that includes a balloon. The balloon has an elastic inner layer and an elastic outer layer. The inner layer and the outer layer are inflatable and deflatable in response to a change of internal pressure of the balloon. The catheter includes a tubular reinforcement member positioned between the inner layer and the outer layer of the balloon in the radial direction of the balloon. At least part of the reinforcement member is not directly fixed to the inner and outer layers. The reinforcement member includes a wire-shaped member. The first end portion and the second end portion of the reinforcement member include ring-shaped inflation restrictors fused to the wire-shaped member. The inflation restrictors restrict inflation of the first and second end portions of the reinforcement member in the radial direction when the inner and outer layers inflate.

12 Claims, 11 Drawing Sheets

(51) Int. Cl.
*B29C 63/00* (2006.01)
*B29C 63/18* (2006.01)
*B29C 69/00* (2006.01)
B29L 31/00 (2006.01)

(52) U.S. Cl.
CPC .......... *B29C 63/0069* (2013.01); *B29C 63/18* (2013.01); *B29C 69/001* (2013.01); *A61M 25/1027* (2013.01); *A61M 25/1034* (2013.01); *A61M 2025/0183* (2013.01); *A61M 2025/1075* (2013.01); *A61M 2025/1084* (2013.01); *A61M 2205/0216* (2013.01); *B29L 2031/7543* (2013.01)

(58) Field of Classification Search
CPC .... A61M 25/10184; A61M 2025/1075; A61M 2025/1084; B29C 63/18
See application file for complete search history.

(56) References Cited

U.S. PATENT DOCUMENTS

2007/0250101 A1\* 10/2007 Horn ................. A61M 25/1029
606/192
2013/0261547 A1 10/2013 Aggerholm et al.
2014/0336689 A1 11/2014 Elton et al.

FOREIGN PATENT DOCUMENTS

| JP | 2014-518739 A | 8/2014 |
|---|---|---|
| WO | WO1996/040350 A1 | 12/1996 |
| WO | WO 2005/120622 A1 | 12/2005 |
| WO | WO 2012/167220 A1 | 12/2012 |

\* cited by examiner

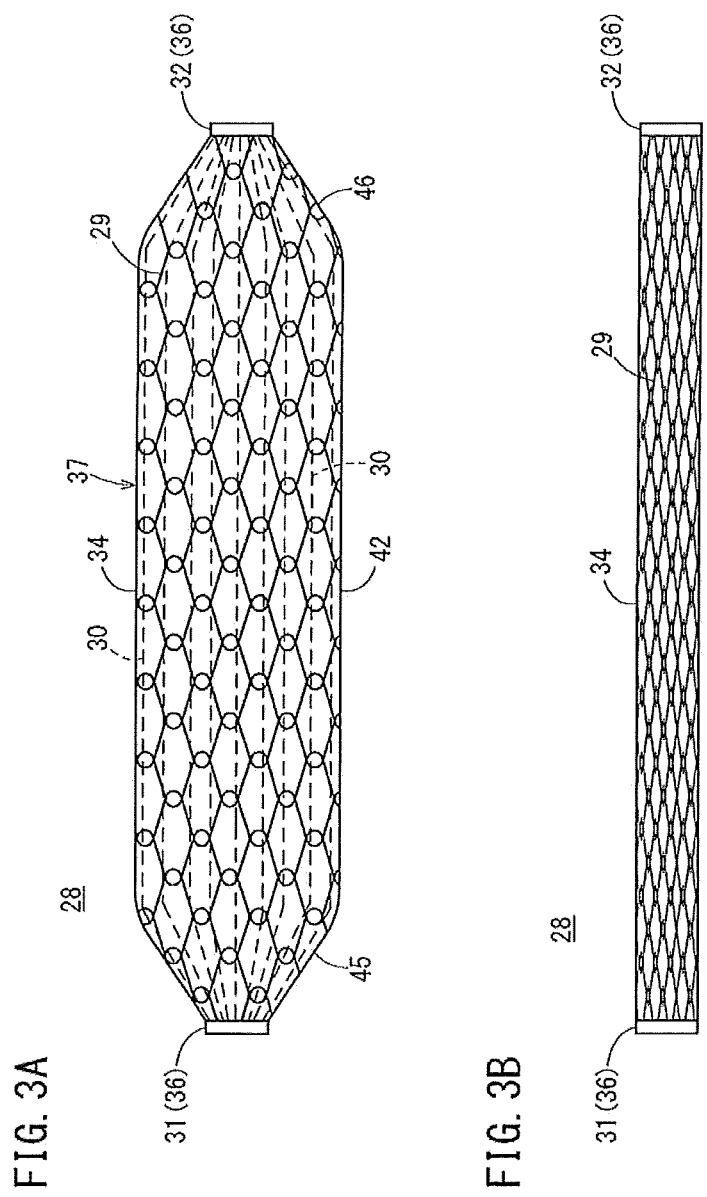

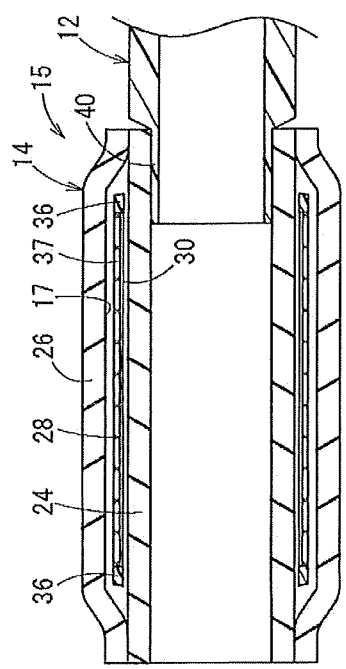 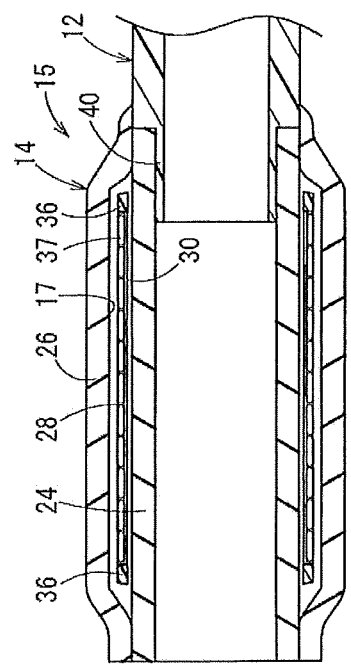
FIG. 7A
FIG. 7B

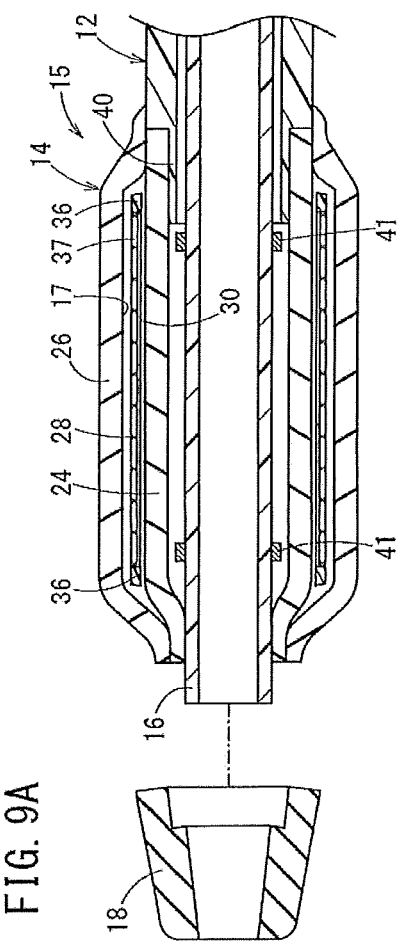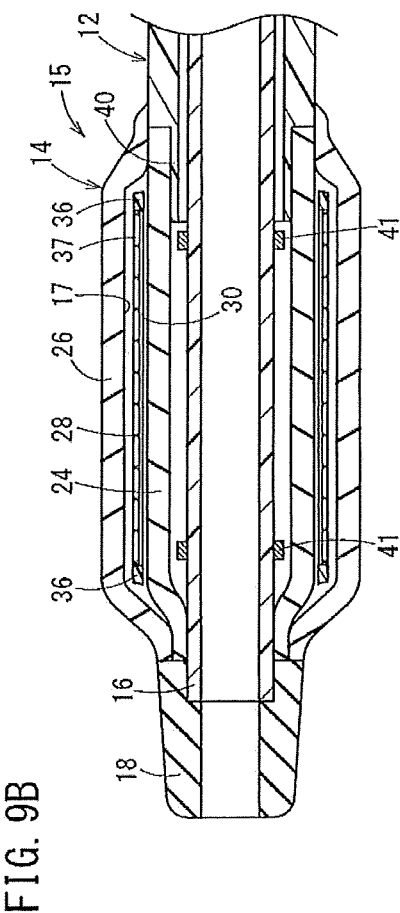
FIG. 9A
FIG. 9B

CATHETER AND METHOD OF MANUFACTURING THE SAME

CROSS-REFERENCES TO RELATED APPLICATIONS

This application is a continuation of International Application No. PCT/JP2015/074625 filed on Aug. 31, 2015, and claims priority to Japanese Patent Application No. 2014-180092, filed on Sep. 4, 2014, the entire contents of both of which are incorporated herein by reference.

TECHNICAL FIELD

The present invention generally relates to a catheter including a balloon reinforced with a reinforcement member, and a method of manufacturing the same.

BACKGROUND ART

Recently, blood flow has been improved by widening a lesion (stenosed portion) of the coronary artery with a balloon catheter, in treatment of, for example, acute myocardial infarction and angina pectoris, percutaneous coronary intervention (percutaneous transluminal coronary angioplasty). For example, refer to Japanese Patent Application Publication No. 2008-501408. Treatment using a balloon catheter may also be performed to improve a lesion formed inside other blood vessels, the bile duct, the trachea, the esophagus, the urethra, and other body lumens.

Generally, a balloon catheter includes a long shaft and a balloon on the distal side of the shaft. The balloon inflates in the radial direction (i.e., expands radially outward by inflation). The balloon catheter is delivered to a stenosed portion in a body after a preceding guide wire is inserted through to the stenosed portion. When the balloon is positioned at the target stenosed portion, the balloon is inflated by pressure-feeding an inflation fluid into the balloon. The stenosed portion can thus be widened.

In order to effectively treat a lesion, the balloon of the balloon catheter is required to have sufficient strength to possess a desired balloon shape when being maximally inflated to widen the lesion. Therefore, in order to apply high-pressure resistance, low compliance properties, and the like to a balloon, a configuration has been proposed in the related art in which a net-shaped reinforcement member is provided in a wall configuring the balloon. For example, refer to Japanese Patent Application Publication No. 2008-501408.

A balloon catheter transports the balloon to a lesion inside the body lumen. Since the balloon needs to pass through the inside of the bent body lumen while being transported, the balloon is required to have flexibility (i.e., be flexible) to follow the bent state of the body lumen. The technology in the related art discussed above, in which a reinforcement member is provided in the wall of the balloon, however, has a problem in flexibility. The problem in flexibility arises because the reinforcement member is integrally fixed to the balloon, and there is no degree of freedom for movement relative to the wall of the balloon. It is thus difficult to apply sufficient flexibility to the balloon.

SUMMARY OF INVENTION

The catheter and catheter manufacturing method disclosed here have been made in consideration of such a problem. The catheter disclosed in this application thus has a balloon reinforced with a reinforcement member that possesses improved flexibility. This application also relates to a catheter manufacturing method for manufacturing this improved catheter.

The catheter disclosed here includes a balloon which has an inner layer and an outer layer. The inner and outer layers possess elastic stretching properties, have tubular shapes, and are able to be inflated and deflated in response to a change of internal pressure. The catheter also includes a tubularly net-shaped reinforcement member positioned between the inner layer and the outer layer and at least a part of which is not directly fixed to the inner layer and the outer layer. The reinforcement member has a first wire-shaped member formed of a high-strength fiber. Both end portions of the reinforcement member in an axial direction are respectively provided with ring-shaped inflation restrictors fused to the first wire-shaped member, and the inflation restriction portions respectively restrict dilation of both the end portions in a circumferential direction. Here, regarding "the reinforcement member", the expression "at least a part of which is not directly fixed to the inner layer and the outer layer" denotes that at least a part of the reinforcement member is not bonded to the inner layer and the outer layer and is not embedded in the inner layer and the outer layer, thereby being able to freely move inside a space formed between the inner layer and the outer layer relative to the inner and outer layers.

The reinforcement member having the first wire-shaped member formed of a high-strength fiber is positioned between the inner layer and the outer layer of the balloon in the radial direction. Therefore, high-pressure resistance and low compliance properties can be suitably applied to the balloon. Here, the term "low compliance properties" denotes balloon characteristics when the balloon is inflated under high pressure, such that the balloon diameter is not unlimitedly widened in response to the pressure and inflation under high pressure can result in a balloon with an appropriate/intended outer diameter. In addition, the term "high-strength fiber" denotes a fiber possessing a tensile break strength equal to or greater than 2 GPa and an elastic modulus equal to or greater than 50 GPa.

The reinforcement member has a degree of freedom for moving relative to the balloon. Therefore, favorable flexibility of the balloon can be maintained. Accordingly, a balloon having high crossability (maneuverability) can be realized even inside a body lumen which meanders/bends in a complicated manner.

When the balloon is inflated, the inflation restriction portions restrict inflation in the circumferential and radial directions of both the end portions of the reinforcement member (i.e., portions at each end of the reinforcement member in the axial direction). The balloon can thus be inflated to have a desired shape inside a body lumen, and a procedure can be effectively performed with respect to a lesion.

The reinforcement member may have a second wire-shaped member formed of a fusible material. The second wire-shaped member may be configured with the same material as the inflation restriction portion. In this configuration, the inflation restriction portion is formed of a fusible material and is fused to the first wire-shaped member. Therefore, the reinforcement member (in which inflation of both the end portions is restricted) can be conveniently manufactured.

A tubularly net-shaped body may be formed of the first wire-shaped member. The multiple second wire-shaped members may be spaced apart in the circumferential direction of the tubularly net-shaped body, and the second wire-shaped members may individually extend along the tubularly net-shaped body from one end portion to the other end portion of the tubularly net-shaped body. The second wire-shaped members may be respectively interlocked with the inflation restriction portions at both of the end portions of the reinforcement member. In this configuration, the tubularly net-shaped body conducting a pressure-resistant function is configured with the first wire-shaped member formed of a high-strength fiber. As a configuration independent from the tubularly net-shaped body, the second wire-shaped member conducting a fusing function is disposed along the tubularly net-shaped body (i.e., extending along the tubularly net-shaped body and in contact with the tubularly net-shaped body). The portion conducting the pressure-resistant function (the first wire-shaped member) and the portion conducting the fusing function (the second wire-shaped member) are established independently from each other. Accordingly, the pressure-resistant function and the fusing function can be individually set. A reinforcement member which has the desired pressure resistance and restricts inflation of both the end portions can thus be simply established (i.e., formed).

The first wire-shaped member and the second wire-shaped member may collectively form the tubularly net-shaped body. In this configuration, the first wire-shaped member and the second wire-shaped member are knitted together to form the tubularly net-shaped body. A base material sleeve is prepared by knitting the first wire-shaped member and the second wire-shaped member, and the base material sleeve is heated and cut. Accordingly, the reinforcement member in which the inflation restriction portions are formed at both the end portions can be simply manufactured.

In the catheter, a cross-sectional area of a cross-section perpendicular to the axial direction in the first wire-shaped member may be greater than a cross-sectional area in the second wire-shaped member. According to the configuration, pressure resistance required in the reinforcement member can be suitably ensured.

The catheter manufacturing method of manufacturing a catheter that includes a balloon which has an inner layer and an outer layer having elastic stretching properties, having tubular shapes, and being able to be inflated and deflated in response to a change of internal pressure, and a tubularly net-shaped reinforcement member which is disposed between the inner layer and the outer layer. The catheter manufacturing method includes a base material sleeve preparation step of preparing a base material sleeve including a first wire-shaped member formed of a high-strength fiber and a second wire-shaped member formed of a fusible material, and a heating and cutting step of heating and cutting multiple spots of the base material sleeve in an axial direction and preparing the reinforcement member in which ring-shaped inflation restriction portions that are formed of fusible materials and are fused to the first wire-shaped member are respectively formed at both end portions in the axial direction.

According to the catheter manufacturing method, the base material sleeve is heated and cut. Therefore, when the reinforcement member having a desired length is cut out from the base material sleeve, the fusible material is fused at the heated portion and the ring-shaped inflation restriction portion fused to the first wire-shaped member is formed. In contrast, when the reinforcement member is configured with only the first wire-shaped member (high-strength fiber), the high-strength fiber is not generally fused and there is little (extremely low) fusing properties. Fibers are thus unlikely to be fused to each other at both the end portions of the reinforcement member, and both the end portions do not perform the restriction function (i.e., restricting expansion in the circumferential and radial directions when the balloon inflates). The reinforcement member of this application in which inflation of both the end portions is restricted can thus be conveniently manufactured.

In another aspect of the catheter manufacturing method, the multiple second wire-shaped members are disposed along the tubularly net-shaped body formed of the first wire-shaped member to be spaced in a circumferential direction of the tubularly net-shaped body when preparing the base material sleeve. Accordingly, the pressure-resistant function and the fusing function can be individually set. Therefore, the reinforcement member which has desired pressure resistance and in which inflation of both the end portions is restricted can be simply established.

In the catheter manufacturing method, outer sides of the multiple second wire-shaped members disposed along an outer surface of a mandrel may be covered with the tubularly net-shaped body when preparing the base material sleeve. Accordingly, the multiple second wire-shaped members are held between the tubularly net-shaped body and the mandrel. Therefore, the reinforcement member can be efficiently prepared.

The first wire-shaped member and the second wire-shaped member may form the tubularly net-shaped base material sleeve. Accordingly, a base material sleeve is prepared by knitting the first wire-shaped member and the second wire-shaped member, and the base material sleeve is heated and cut. Accordingly, the reinforcement member (in which the inflation restriction portions are formed at both the end portions) can be simply manufactured.

The base material sleeve may be formed such that a cross-sectional area of a cross-section perpendicular to the axial direction of the base material sleeve in the first wire-shaped member is greater than a cross-sectional area in the second wire-shaped member. Accordingly, pressure resistance required of that in the reinforcement member can be suitably ensured.

Flexibility of the balloon reinforced with the reinforcement member can be improved in the catheter described above.

In another aspect, this application involves a catheter including an elongated shaft extending in an axial direction and a balloon connected to the elongated shaft. The balloon includes an elastic inner layer and an elastic outer layer. The inner layer and the outer layer are tubularly shaped and are inflatable and deflatable in a radial direction in response to a change of internal pressure of the balloon. The catheter includes a tubular reinforcement member positioned between the inner layer and the outer layer of the balloon in the radial direction. At least part of the reinforcement member is movable relative to the inner layer and the outer layer. The reinforcement member includes a first wire-shaped member and possesses a first end portion and a second end portion opposite the first end portion in the axial direction. The first end portion and the second end portion of the reinforcement member are both ring-shaped inflation restrictors fused to the first wire-shaped member. The inflation restrictors restrict inflation of both the first and second end portions of the reinforcement member in the radial direction when the inner and outer layers inflate in the radial direction in response to the change of internal pressure of the balloon. The reinforcement member is configured to restrict inflation of the inner layer and the outer layer of the balloon so that the balloon possesses a cylindrically-shaped outer diameter intermediate portion when the balloon is fully inflated.

BRIEF DESCRIPTION OF THE DRAWINGS

FIG. 3A is a side view illustrating a reinforcement member when inflated, and

FIG. 3B is a side view illustrating the reinforcement member when deflated.

FIG. 7A illustrates the distal end of a shaft and the proximal end of a balloon being joined to each other, and FIG. 7B is a second view illustrating the distal end of the shaft and the proximal end of the balloon being joined to each other.

FIG. 9A illustrates a distal tip and the inner tube being joined to each other, and FIG. 9B is a second view illustrating the distal tip and the inner tube being joined to each other.

DESCRIPTION OF EMBODIMENT

Set forth below with reference to the accompanying drawings is a detailed description of embodiments of a catheter and a method for manufacturing a catheter representing examples of the inventive catheter and method disclosed here.

Figure 1:
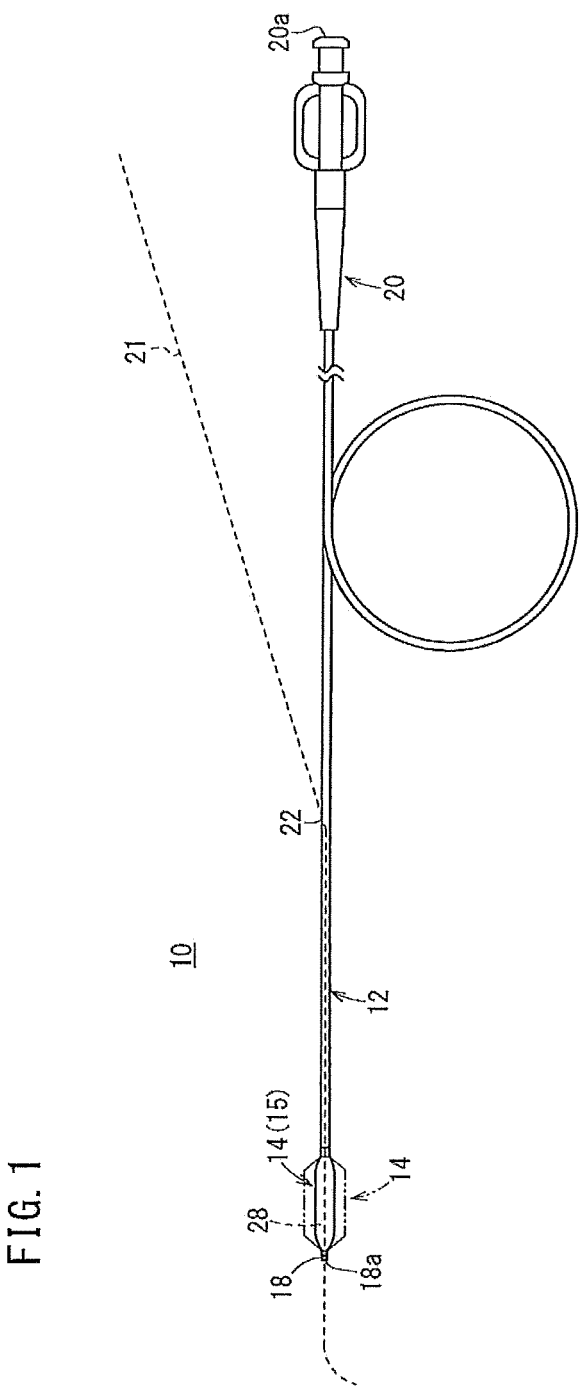
FIG. 1 is a partially-omitted schematic view illustrating a first embodiment of a catheter disclosed here.

FIG. 1 is a partially-omitted schematic view illustrating a configuration of a catheter 10 according to the embodiment. The catheter 10 is a so-called PTCA (percutaneous transluminal coronary angioplasty: percutaneous coronary intervention) inflation catheter for performing treatment in a living body. The catheter 10 includes a long shaft 12 which is inserted through a biological organ (for example, the coronary artery) and a balloon 14 on the distal side of the long shaft 12 which may be inflated at a stenosed portion (lesion). The stenosed portion is thereby widened.

The aspects of the catheter described here can also be applied to a catheter other than a PTCA dilation catheter. For example, the catheter can be for improving a lesion formed inside biological organs such as other blood vessels, the bile duct, the trachea, the esophagus, the urethra, and other internal organs.

Figure 2:
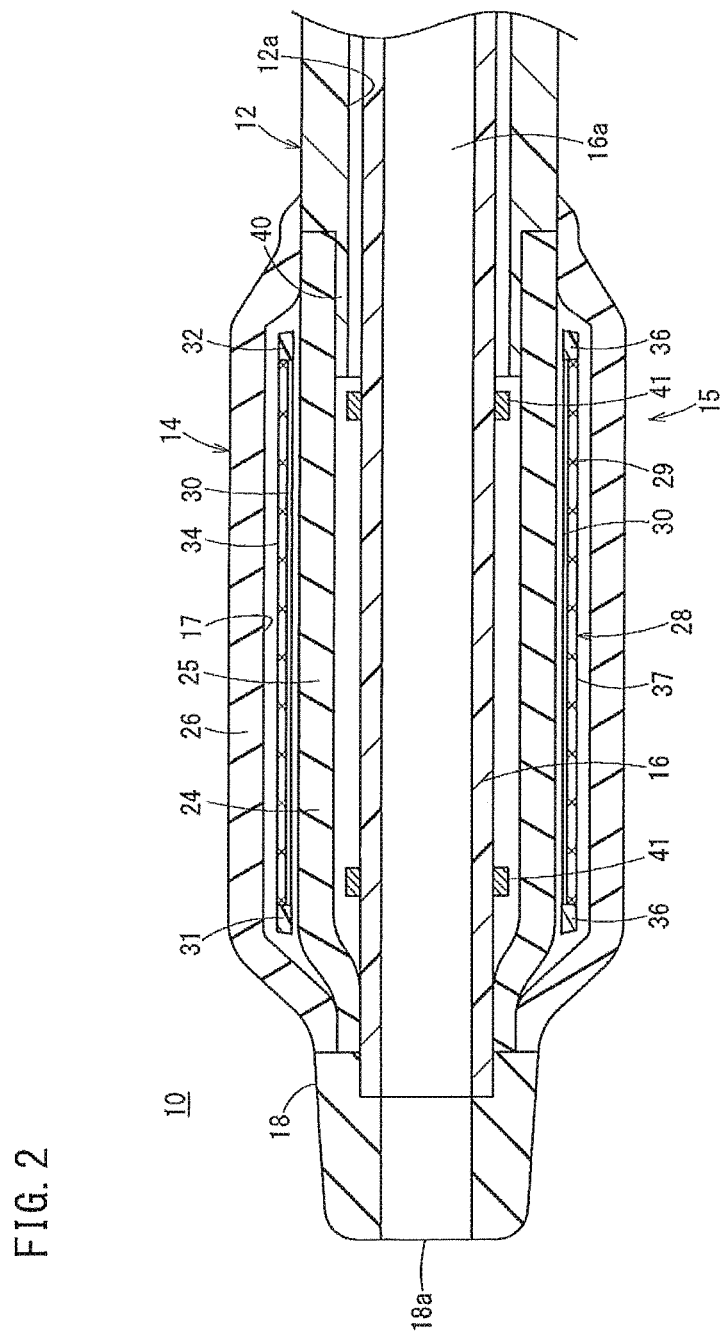
FIG. 2 is a schematic cross-sectional view of the distal portion of the catheter illustrated in FIG. 1.

As illustrated in FIGS. 1 and 2, the catheter 10 includes the long shaft 12 possessing a small diameter, the balloon 14 joined to the distal end of the shaft 12, a reinforcement member 28 disposed inside a membrane (wall) configuring the balloon 14, an inner tube 16 inserted through the shaft 12 and the balloon 14, a distal tip 18 joined to the distal end of the balloon 14, and a hub 20 on the proximal side of the shaft 12.

The catheter 10 illustrated in FIG. 1 is a so-called "rapid exchange-type" catheter provided with an opening portion 22 through which a guide wire 21 is guided (i.e., through a middle portion of the shaft 12 in a longitudinal direction). In another embodiment, the catheter 10 may be an "over-the-wire-type" catheter in which a guide wire lumen is formed throughout the overall length of the catheter 10, and the guide wire 21 is guided through the proximal end of the hub 20.

The shaft 12 is a flexible tube with two open ends (i.e., both ends in an axial direction are open). The shaft 12 is relatively long and has a relatively small outer diameter. The shaft 12 extends from the rear end of the balloon 14 to the distal end of the hub 20. A portion from the distal end to the opening portion 22 is a double tube which forms an inflation lumen 12a between the shaft 12 and the inner tube 16. A portion between the opening portion 22 and the hub 20 is a single tube. Inflation fluid for the balloon 14 is supplied through the inflation lumen 12a formed in the shaft 12.

In the shaft 12, the inflation fluid can be fed under pressure to the balloon 14 from a pressure applying apparatus such as an indeflator (not illustrated) connected via a luer taper 20a or the like provided in the hub 20. For example, the inflation fluid may be a contrast agent, a physiological salt solution, or a mixture of these fluids.

The inner tube 16 is a guide wire tube forming a wire lumen 16a through which the guide wire 21 is inserted. The distal end of the inner tube 16 is positioned on the distal side beyond the proximal end of the distal tip 18 (i.e., the distal-most end of the inner tube 16 is distal to the proximal-most end of the distal tip 18). The inner tube 16 extends inside the balloon 14 and the shaft 12. The proximal end of the inner tube 16 is liquid-tightly joined to the opening portion 22 (refer to FIG. 1). The opening portion 22 is formed in an intermediate portion of the shaft 12. Therefore, the guide wire 21 can be inserted through a distal end opening portion 18a serving as an entrance at the distal tip 18, through the wire lumen 16a of the inner tube 16 from the distal side toward the proximal side and out through the opening portion 22 serving as an exit.

It is favorable to provide a radiopaque marker 41 on the inner tube 16 inside the balloon 14. The radiopaque marker 41 is configured with an X-ray opaque (radiopaque) material (for example, gold, platinum, tungsten, or a mixture of these metals). The radiopaque marker 41 is used for visually recognizing the position of the balloon 14 in a living body under an X-ray contrast condition. The radiopaque marker 41 can be configured, for example, to have a tubular shape (ring shape). As illustrated in FIG. 2, multiple radiopaque markers 41 may be provided on the outer surface of the inner tube 16 inside the balloon 14 while being spaced apart from each other in the axial direction. In another embodiment, only one radiopaque marker 41 may be provided on the inner tube 16 inside the balloon 14.

It is preferable that the shaft 12 and the inner tube 16 have structures with appropriate flexibility and appropriate rigidity such that an operator can smoothly insert the long catheter 10 into a biological organ (such as a blood vessel) while grasping and operating the proximal side of the catheter 10. For example, it may thus be favorable that the shaft 12 and the inner tube 16 are formed of a polymeric material such as polyolefin (for example, polyethylene, polypropylene, polybutene, an ethylene-propylene copolymer, an ethylene-vinyl acetate copolymer, ionomer, and a mixture of two or more types of these materials), polyvinyl chloride, polyamide, a polyamide elastomer, polyurethane, a polyurethane elastomer, polyimide, and a fluorine resin, or a mixture thereof; or a multi-layer tube including two or more types of these materials.

The balloon 14 can be inflated and dilated in response to a change of internal pressure (i.e., the balloon 14 is configured to expand and to deflate). The distal portion of the balloon 14 is joined to a portion in the vicinity of the distal portion of the inner tube 16, and the proximal portion of the balloon 14 is joined to the distal portion of the shaft 12 (e.g., the outer surface of the distal portion of the shaft 12 as shown in FIG. 2). The internal space of the balloon 14 communicates with the inflation lumen 12a.

The inflation fluid can flow into (be guided into) the balloon 14 via the inflation lumen 12a. The inflation fluid can also be discharged from the balloon 14 via the inflation lumen 12a. The balloon 14 inflates when the inflation fluid is guided into the balloon 14. As indicated by the imaginary line in FIG. 1, a portion between the distal end and the proximal end of the balloon exhibits a shape which is increased in diameter and has a substantially uniform outer diameter along the axial direction when the balloon 14 is maximally inflated.

The balloon 14 is required to have appropriate flexibility to pass through a meandering or bent point of a body lumen. The balloon 14 is also required to have strength to the extent that a lesion can be reliably widened and needs to have high-pressure resistance and low compliance properties (i.e., the balloon 14 does not inflate beyond an intended outer diameter). The balloon 14 illustrated in FIG. 2 has an inner layer 24 and an outer layer 26 having tubular shapes, having elastic stretching properties, and configuring fluid-impermeable balloon walls. The reinforcement member 28 is disposed between the inner layer 24 and the outer layer 26 (i.e., in the radial direction). The balloon 14 and the reinforcement member 28 configure a dilation portion 15 (inflation portion) which can be inflated and deflated in a radial direction at the distal portion of the catheter 10.

The inner layer 24 transfers force to the reinforcement member 28 in response to the inflation fluid being guided into the balloon 14 (pressurization). The inner layer 24 expands to the extent of a shape which is restricted along the inflated shape of the reinforcement member 28. The outer layer 26 expands along the inflated shape of the reinforcement member 28 in response to the inflation fluid guided into the balloon 14 (pressurization). The outer layer 26 contracts to the initial shape (i.e., the pre-pressurized shape) in response to the inflation fluid being discharged from the inside of the balloon 14 (decompression), which restores the original shape (position) of the reinforcement member 28 before being inflated. Therefore, it is preferable that the outer layer 26 is formed of a base material having a high stretching recovery rate.

The inner layer 24 and the outer layer 26 are joined to each other at the distal portions and the proximal portions of each of the respective inner layer 24 and outer layer 26, for example, through fusing or bonding. An annularly sealed accommodation chamber 17 is formed between the inner layer 24 and the outer layer 26. The accommodation chamber 17 is a chamber radially between the outer surface of the inner layer 24 and the inner surface of the outer layer 26 that accommodates the reinforcement member 28.

Examples of the inner layer 24 and the outer layer 26 materials include various types of rubber material such as natural rubber, butyl rubber, isoprene rubber, butadiene rubber, styrene-butadiene rubber, and silicone rubber; various types of thermoplastic elastomer such as a polyurethane-based elastomer, a polyester-based elastomer, a polyamide-based elastomer, an olefin-based elastomer, and a styrene-based elastomer; mixtures of these materials; and the like. The material of the inner layer 24 and the material of the outer layer 26 may be the same as each other or may be different from each other.

The reinforcement member 28 is a tubularly net-shaped (e.g., mesh) member. The reinforcement member 28 is positioned between the inner layer 24 and the outer layer 26 such that at least a part of the reinforcement member 28 is movable relative to the balloon 14, and the reinforcement member 28 functions to enhance pressure resistance of the balloon 14.

The reinforcement member 28 includes two end portions (first end portion 31 and second end portion 32) opposite one another in the axial direction and an intermediate portion 34 between the first end portion 31 and the second end portion 32. The intermediate portion 34 is not directly fixed to both the inner layer 24 and the outer layer 26 and at least one of the first end portion 31 and the second end portion 32 is not directly fixed to both the inner layer 24 and the outer layer 26. Accordingly, movement of the reinforcement member 28 relative to the inner layer 24 and the outer layer 26 in the axial direction and a circumferential direction is allowed.

The inner layer 24 and the outer layer 26 may be fixedly attached (for example, fused or bonded) via a gap (mesh) between first threads 29 forming the reinforcement member 28. Accordingly, while the reinforcement member 28 is allowed to move relative to the inner layer 24 and the outer layer 26 to a certain extent in the axial and/or radial directions, the moving range of the reinforcement member 28 can be restricted.

In the embodiment illustrated in FIG. 2, the other one of the first end portion 31 and the second end portion 32 is also not directly fixed to the inner layer 24 and the outer layer 26 (i.e., both the first end portion 31 and the second end portion 32 are not directly fixed to the inner layer 24 and the outer layer 26 in the FIG. 2 embodiment). Accordingly, the reinforcement member is allowed to move relative to the inner layer 24 and the outer layer 26 in the axial direction. In other words, the reinforcement member 28 is not fixed to any one of the inner layer 24 and the outer layer 26 in the present embodiment. Therefore, the reinforcement member 28 can freely move in the circumferential direction and the axial direction within the accommodation chamber 17 between the outer surface of the inner layer 24 and the inner surface of the outer layer 26 (within the range restricted between the inner layer 24 and the outer layer 26).

Only one of the first end portion 31 or the second end portion 32 may be fixed to the inner layer 24 and the outer layer 26 (i.e., the other of the first end portion 31 and the second end portion 32 is not fixed to the inner layer 24 and to the outer layer 26). The fixing means to fix the end portion (i.e., either the first end portion 31 or the second end portion 32) to the inner layer 24 and outer layer 26 is not limited to any particular means and suitable fixing means such as fusing and bonding may be employed.

The reinforcement member 28 has the first thread 29 (first wire-shaped member) formed of a high-strength fiber, and a second thread 30 (second wire-shaped member) formed of a fusible material. Both the end portions 31, 32 of the reinforcement member 28 in the axial direction are respectively provided with ring-shaped inflation restriction portions 36 (ring-shaped inflation restrictors) which are formed of fusible materials and are fused (e.g., by applying heat) to the first thread 29. The inflation restriction portions 36 restrict inflation of each of the end portions (first end portion 31 and second end portion 32) in the circumferential direction.

One or more first threads 29 form a tubularly net-shaped body 37 as illustrated in FIG. 3A. The tubularly net-shaped body 37 is formed by knitting (weaving) one or more first threads 29. The tubularly net-shaped body 37 has stretching properties (i.e., is stretchable/expandable) in at least the circumferential direction (and the radial direction).

The method of forming the tubularly net-shaped body 37 is not limited to any particular form. Examples of the forming method include tube-knitting and braiding. In a case of tube-knitting, the first threads 29 extending in the circumferential direction in a waved manner are arranged in the axial direction, and the waved first threads 29 adjacent to each other in the axial direction are interlaced with each other (refer to FIG. 3A) to form the tubularly net-shaped body 37. In a case of braiding, one or more first threads 29 extending in a first spiral direction and one or more first threads 29 extending in a second spiral direction are woven so as to intersect each other, thereby forming the tubularly net-shaped body 37.

The high-strength fiber denotes a fiber possessing a tensile break strength equal to or greater than 2 GPa and an elastic modulus equal to or greater than 50 GPa. The high-strength fiber is also referred to as a super fiber. It is preferable that the first thread 29 is a twisted thread formed of the high-strength fiber. Examples of the high-strength fiber include an aramid fiber, a carbon fiber, a polyarylate fiber, a PBO fiber, ultra-high molecular weight polyethylene, and an LCP fiber. Generally, since the high-strength fiber is not fused even when being heated, there are no fusing properties or extremely low fusing properties relative to other members (i.e., the high-strength fiber does not fuse with the other members, such as the second wire-shaped member, when being heated).

For example, the outer diameter of the first thread 29 may range approximately from 5 to 100 μm. When the twisted thread formed of high-strength fibers is used as the first thread 29, for example, a single fiber outer diameter of the high-strength fiber may range approximately from 5 to 30 μm. For example, a single fiber outer diameter of 12 μm can be used for the high-strength fiber. However, a thinner fiber may be used or a thicker fiber may be used. When using a thicker fiber, it is favorable to employ a loosely twisted thread that is in an unraveled state when tensile force is not applied to the twisted thread.

Multiple second threads 30 formed of fusible materials are positioned in the reinforcement member 28 to be spaced apart from one another in the circumferential direction of the tubularly net-shaped body 37. Here, "fusible material" denotes a material which can be softened and fused by being heated to a predetermined temperature or higher, and the fusible material has fusing properties with respect to other members (i.e., the fusible material can be fused/welded to other members).

The second threads 30 individually extend along the tubularly net-shaped body 37 in the axial direction from one end portion to the other end portion of the tubularly net-shaped body 37. The second threads 30 are each interlocked with the inflation restriction portions 36 at both of the end portions 31, 32 of the reinforcement member 28. The second thread 30 is not bonded and is not fused to the tubularly net-shaped body 37 (first thread 29) in a region between the inflation restriction portions 36. Therefore, the second thread 30 is not fixed in this region.

The inflation restriction portion 36 is formed during the process of manufacturing the reinforcement member 28. The inflation restriction portion 36 is formed by fusing the multiple second threads 30 which are arranged (spaced apart) in the circumferential direction. The fused material flows in the circumferential direction and is solidified thereafter to form each of the inflation restriction portions 36. The number of the second threads 30, disposition spaces in the circumferential direction, the thickness, and/or the like are set such that the fused material is connected to form the ring shaped inflation restriction portion 36 in accordance with fusion and flowing when the second threads 30 are heated and the fused material has strength (rigidity) to the extent that inflation of both the end portions of the reinforcement member 28 can be reliably restricted.

Examples of the material (fusible material) of the second thread 30 include polyvinyl chloride, polyethylene, polypropylene, annular polyolefin, polystyrene, poly-(4-methylpentene-1), polycarbonate, an acrylic resin, an acrylonitrile-butadiene-styrene copolymer, polyester such as polyethylene terephthalate and polyethylene naphthalate, a butadiene-styrene copolymer, a polyamide (for example, nylon 6, nylon 6.6, nylon 6.10, and nylon 12), and a polyamide elastomer.

Figure 4A:
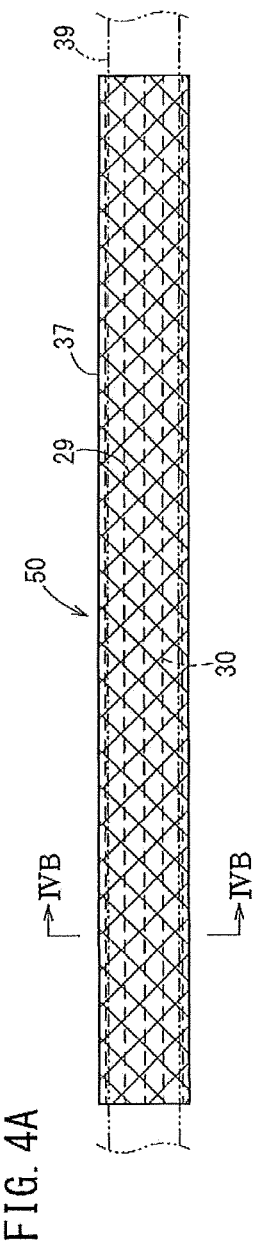
FIG. 4A illustrates a base material sleeve being prepared.
Figure 4B:
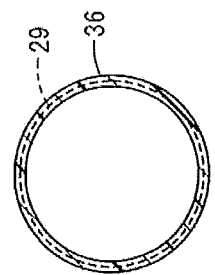
FIG. 4B is a cross-sectional view taken along line IVB-IVB in FIG. 4A.
Figure 4C:
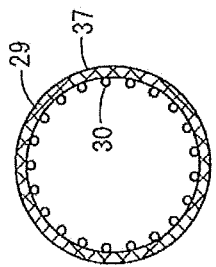
FIG. 4C is a cross-sectional view of a fused portion of the base material sleeve.

The second threads 30 of the embodiment illustrated in FIG. 4B are disposed on the inner surface side of the tubularly net-shaped body 37. However, the second threads 30 may be disposed on the outer surface side of the tubularly net-shaped body 37.

As illustrated in FIG. 2, each of the second threads 30 may extend along the axial direction of the reinforcement member 28 (i.e., longitudinally) when the balloon 14 is deflated. Alternatively, each of the second threads 30 may extend in a direction tilting with respect to the axial direction of the reinforcement member 28 (that is, in a spiral manner).

As illustrated in FIG. 2, the distal portion of the inner layer 24 is joined to the outer surface of the inner tube 16. The proximal portion of the inner layer 24 is joined to the outer surface of the distal portion (thin portion 40) of the shaft 12. The outermost distal portion of the thin portion 40 of the shaft 12 is positioned distally beyond the innermost proximal surface of the inner layer 24, on the inner side of the inner layer 24 (the outer surface of the thin portion 40 faces the inner surface of the inner layer 24 at a proximal portion of the inner layer 24). Therefore, a stretchable region (hereinafter, will be referred to as "stretchable region 25 of the inner layer 24") in the inner layer 24 during deformation of inflation and deflation of the balloon 14 is between a joint spot (i.e., the joining location) of the inner layer 24 and the inner tube 16, and the outermost distal portion of the thin portion 40 of the shaft 12.

The innermost proximal portion (i.e., the proximal-most end) of the reinforcement member 28 is positioned proximally beyond the innermost proximal portion (i.e., the proximal-most end) of the stretchable region 25 in the inner layer 24. As illustrated in FIG. 2, the second end portion 32 of the reinforcement member 28 may be proximally beyond the distal-most end of the thin portion 40 of the shaft 12 in the accommodation chamber 17 formed between the inner layer 24 and the outer layer 26 of the balloon 14. Accordingly, when the balloon 14 is dilated, the second end portion 32 of the reinforcement member 28 is less affected by inflation of the balloon 14 and contributes to the restriction of the maximally inflated diameter of the balloon 14 performed by the reinforcement member 28.

FIG. 3A is a side view illustrating the reinforcement member 28 when inflated, and FIG. 3B is a side view illustrating the reinforcement member 28 when deflated. As illustrated in FIG. 3A, when the reinforcement member 28 is inflated in the circumferential direction, the first threads 29 are in a tensed state, and the outer diameter of the reinforcement member 28 is not increased beyond a certain extent. Since inflation of the first end portion 31 and the second end portion 32 is restricted, the shape of the reinforcement member 28 (intermediate portion 34) when being inflated includes a straight portion 42 having a substantially uniform outer diameter and outer-diameter varying portions (tapered portions) 45 and 46 which are respectively positioned on both sides of the straight portion 42 in the axial direction and decrease in outer diameter from the straight portion 42 to the respective end portion (i.e., the first end portion 31 or the second end portion 32) in the axial direction.

When the balloon 14 contains the reinforcement member 28 illustrated in FIGS. 3A and 3B, the balloon 14 includes a straight portion having a substantially uniform outer shape due to the reinforcement member 28 (i.e., the reinforcement member 28 is configured to restrict inflation of the inner layer and the outer layer of the balloon 14 so that the balloon 14 possesses a cylindrically-shaped outer diameter intermediate portion when the balloon 14 is fully inflated) and outer-diameter varying portions (tapered portions) which are respectively positioned on both sides of the straight portion and are decreased in outer diameter in the axial direction when the balloon 14 is inflated. The radiopaque marker 41 is disposed on the inner tube 16 such that the position of the straight portion of the balloon 14 can be perceived. Accordingly, positioning the region of the maximally inflated diameter in the balloon 14 relative to the lesion can be easily performed because an operator can visually recognize the position having the maximally inflated diameter in the balloon 14 under an X-ray contrast condition.

When the reinforcement member 28 having the tubularly net-shaped body 37 is formed through the knitting method in which the waved first threads 29 adjacent to each other in the axial direction are interlaced with each other, the first threads 29 are folded and the reinforcement member 28 (tubularly net-shaped body 37) is decreased in outer diameter when the reinforcement member 28 is compressed in the circumferential direction as illustrated in FIG. 3B. When the reinforcement member 28 is compressed in the axial direction, the first threads 29 of the meshes become misaligned and the first threads 29 adjacent to each other in the axial direction can overlap each other. Moreover, the reinforcement member 28 can be bent in accordance with rotations of the interlaced portion between the first threads 29 adjacent to each other in the axial direction. Therefore, the reinforcement member 28 has excellent flexibility with respect to bending.

In FIGS. 1 and 2, the distal tip 18 provided on the distal side of the balloon 14 is a distal-most portion of the catheter 10 which flexibly advances through a curved portion, an irregular portion, and the like inside a biological organ, penetrates a lesion (stenosed portion), and leads the catheter 10 to be smoothly inserted through the lesion. The distal tip 18 is a short tube having an inner diameter substantially the same as the inner diameter of the inner tube 16.

The distal tip 18 is fitted to the distal portion of the inner tube 16 from the outside so as to be liquid-tightly joined to the distal portion of the inner tube 16 (the distal tip 18 is fixed to the outer surface and distal-most face of the inner tube 16 as illustrated in FIG. 2). The distal tip 18 protrudes toward the distal side beyond the opening portion of the wire lumen 16a. The proximal surface of the distal tip 14 (i.e., the surface at the proximal-most end of the distal tip 14) is joined to the distal surface of the balloon 14. The distal end opening portion 18a of the distal tip 18 communicates with the wire lumen 16a of the inner tube 16 and serves as the entrance of the guide wire 21.

The material and the shape of the distal tip 18 are suitably selected such that the distal tip 18 is configured to be more flexible than at least the shaft 12 and the inner tube 16. Note that, the distal tip 18 may be omitted in some embodiments. When the distal tip 18 is omitted, it is favorable to employ a configuration in which the outermost distal end position of the inner tube 16 and the outermost distal end position of the balloon 14 coincide with each other, or a configuration in which the outermost distal end position of the inner tube 16 slightly protrudes beyond the outermost distal end position of the balloon 14.

An example of a method of manufacturing the catheter 10 (mainly, a step of manufacturing the dilation portion 15 and peripheral portions of the dilation portion 15) will now be described. Note that, the disclosed method of manufacturing the catheter 10 is not limited to any exemplified manufacturing method described here. In FIGS. 4A to 9B, the tubularly net-shaped body 37 is schematically illustrated, and the tubularly net-shaped body 37 is not limited to any particular knitting method.

FIGS. 4A to 4D are views illustrating steps of manufacturing the reinforcement member 28. First, a step of preparing a tubularly net-shaped base material sleeve 50 which becomes the base material of the reinforcement member 28 (base material sleeve preparation step) is executed as illustrated in FIG. 4A. The base material sleeve 50 has a length equal to or greater than those of multiple reinforcement members 28.

In the base material sleeve preparation step, specifically, multiple second threads 30 are positioned/applied along the tubularly net-shaped body 37 formed of the first thread 29 to be spaced apart from one another in the circumferential direction of the tubularly net-shaped body 37 (see also FIG. 4B which is a cross-sectional view taken along line IVB-IVB in FIG. 4A). It is favorable that the multiple second threads 30 be spaced apart in the circumferential direction along the outer surface of a mandrel 39 and the outer sides of the disposed multiple second threads 30 are covered with the tubularly net-shaped body 37 as illustrated in FIG. 4A. Accordingly, multiple second threads 30 can be held between the tubularly net-shaped body 37 and the mandrel 39. There is thus no need to provide a separate mechanism for holding the second threads 30, and the second threads 30 can be appropriately and efficiently positioned on the tubularly net-shaped body 37.

Figure 4D:
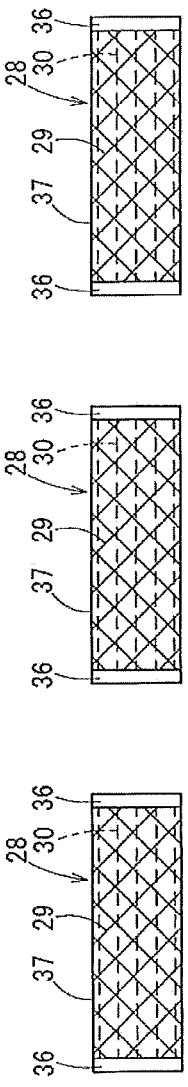
FIG. 4D is a view describing a step of preparing the multiple reinforcement members from the base material sleeve.

The catheter manufacturing method next includes heating and cutting multiple spots of the base material sleeve 50 in the axial direction, thereby executing a step of preparing one or more reinforcement members 28 (multiple reinforcement members 28 as illustrated in FIG. 4D). In each of the reinforcement members 28 heat and cut in this manner, the ring-shaped inflation restriction portions 36 are formed of fusible materials and are fused to the first thread 29. The ring-shaped inflation restriction portions 36 are formed at both end portions of each reinforcement member 28 in the axial direction (heating and cutting step) as illustrated in FIG. 4D.

As described, the base material sleeve 50 is heated and cut. Accordingly, when the reinforcement member 28 is cut out (at a desired length) from the base material sleeve 50 and the second threads 30 are fused at the heated portion, the fused material flows and spreads in the circumferential direction of the base material sleeve 50. As a result of these actions, a change occurs in the structure at the heated portion as illustrated in the progression between FIGS. 4B and FIG. 4C, and the ring-shaped inflation restriction portions 36 fused to the first thread 29 are formed.

Figure 5A:
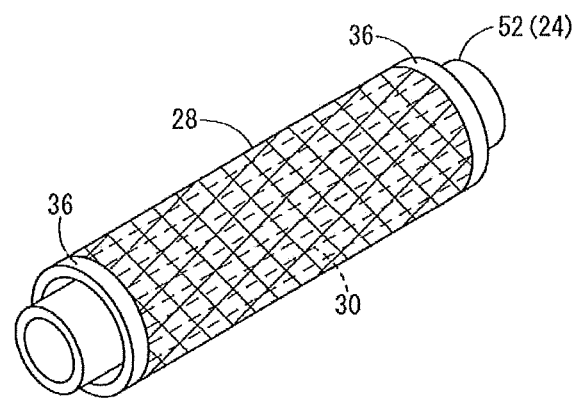
FIG. 5A illustrates an inner layer tube being covered with the reinforcement member.

Subsequently, the inner layer tube 52, which is the base material of the inner layer 24, is covered by the reinforcement member 28 (first covering step) as illustrated in FIG. 5A. Both end portions of the inner layer tube 52 may respectively protrude beyond openings at both ends of the reinforcement member 28 as shown in FIG. 5A.

Figure 5B:
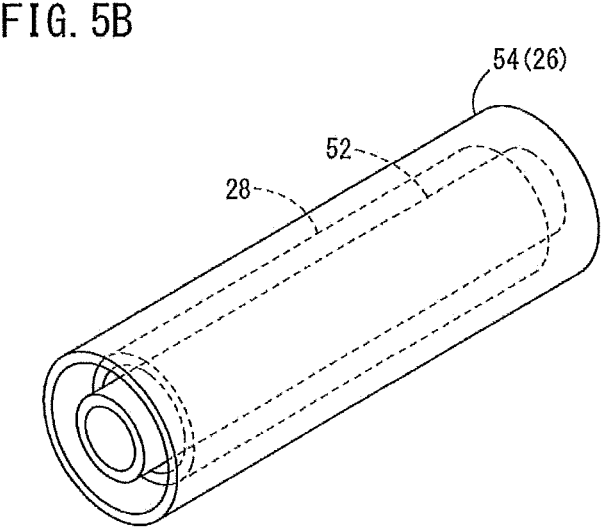
FIG. 5B illustrates the inner layer tube and the reinforcement member being covered with an outer layer tube.

The inner layer tube 52 and the reinforcement member 28 (i.e., the reinforcement member 28 in a state where the inner layer tube 52 is inserted within the interior of the reinforcement member 28) are then covered by an outer layer tube 54 (second covering step). The outer layer tube 54 is the base material of the outer layer 26. As shown in FIG. 5B, the inner layer tube 52 and the reinforcement member 28 are covered by the outer layer tube 54 such that the overall length of the reinforcement member 28 is housed inside the outer layer tube 54 (both end portions of the outer layer 26 protrude in the axial direction beyond both of the end portions of the reinforcement member 28).

Figure 6A:
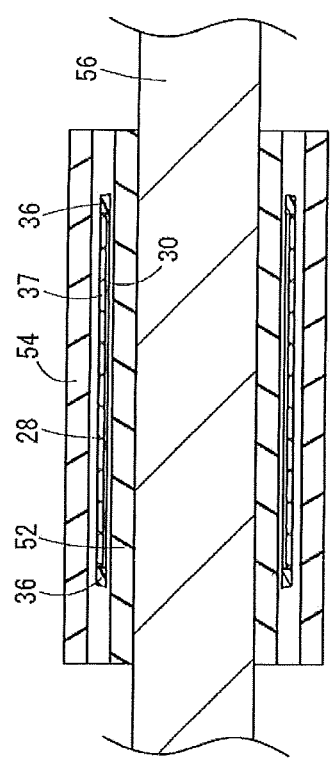
FIG. 6A illustrates the inner layer tube and the outer layer tube being joined to each other.
Figure 6B:
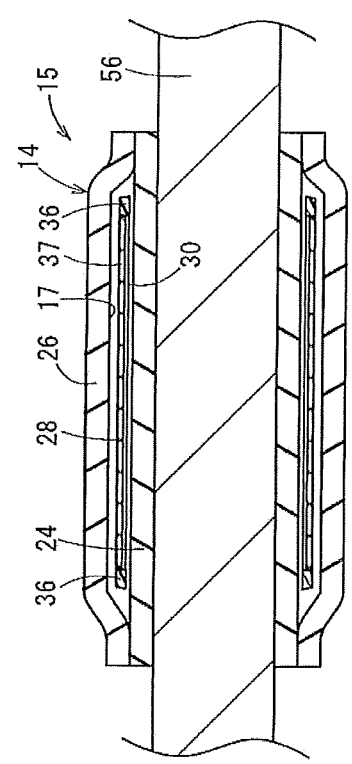
FIG. 6B is a second view illustrating the inner layer tube and the outer layer tube being joined to each other.

A step of joining the inner layer tube 52 and the outer layer tube 54 (step of joining inner and outer layers) is next executed. As illustrated in FIG. 6A, a mandrel 56 (core bar) is inserted into the inner layer tube 52 (i.e., into the interior of the assembly of the inner layer tube 52, the outer layer tube 54, and the reinforcement member 28). One end portion of the inner layer tube 52 and one end portion of the outer layer tube 54 are then fused to be joined to each other at one end portions and the other end portions. Accordingly, the annularly sealed accommodation chamber 17 is created between the inner layer 24 and the outer layer 26, thereby obtaining the dilation portion 15 in a state where the reinforcement member 28 is located inside the accommodation chamber 17. After the step of joining inner and outer layers, the mandrel 56 is removed.

In the present embodiment, the reinforcement member 28 is merely disposed inside the accommodation chamber 17 and is not joined to other members through fusing, bonding, or the like. Therefore, the reinforcement member 28 is not fixed to any portion of the balloon 14 (i.e., to the inner layer 24 and outer layer 26).

Subsequently, a step of joining the balloon 14 (dilation portion 15) and the shaft 12 to each other (step of joining a balloon and a shaft) is executed as illustrated in FIGS. 7A and 7B. The thin portion 40 is first formed at the distal portion of the shaft 12. To form the thin portion 40, for example, the distal portion of the shaft 12 is drawn down (the mandrel is inserted into a hollow portion of the shaft 12, and the distal portion of the shaft 12 is pressedly input into a mold which includes a hole having a diameter smaller than that of the shaft 12). Therefore, the distal portion can have a relatively small outer diameter (e.g., smaller than the outer diameter of the rest of the shaft 12). The thin portion 40 of the shaft 12 is inserted into the interior of the proximal side of the balloon 14 as shown in FIG. 7A. Subsequently, as illustrated in FIG. 7B, the proximal portion of the balloon 14 and the distal portion (thin portion 40) of the shaft 12 are fused to be joined to each other.

Figure 8A:
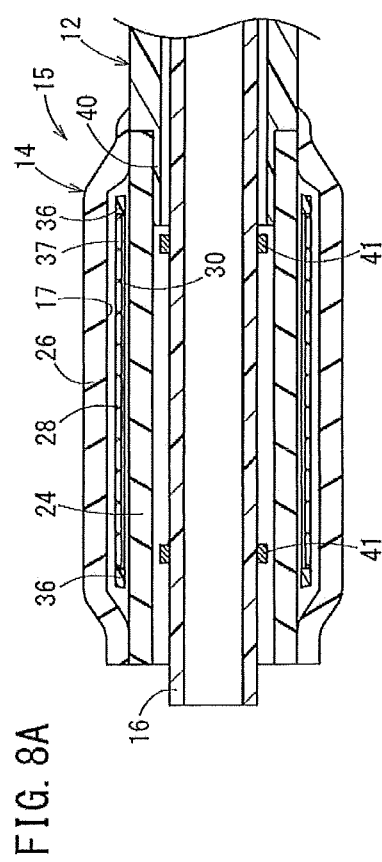
FIG. 8A illustrates an inner tube and the distal end of the balloon being joined to each other.

Even though the step is not illustrated, the radiopaque marker 41 is attached to the outer surface of the inner tube 16 (the attached radiopaque marker 41 is shown in FIG. 8A). Specifically, the tubular radiopaque marker 41 having an inner diameter slightly greater than the inner tube 16 is moved around the outer side of the inner tube 16, and the mandrel is inserted into the inner tube 16. Thereafter, the entire circumference of the radiopaque marker 41 is beaten (swaging step). The inner diameter of the radiopaque marker 41 is thus decreased to contact/engage with the outer surface of the inner tube 16. In this manner, the radiopaque marker 41 is fixed to the inner tube 16.

Figure 8B:
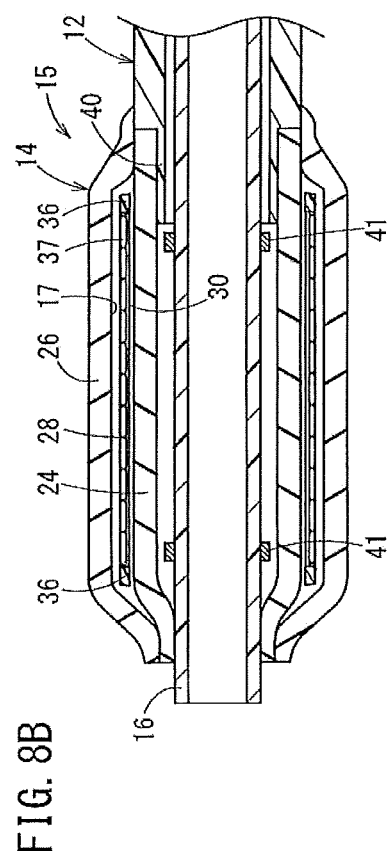
FIG. 8B is a second view illustrating the inner tube and the distal end of the balloon being joined to each other.

The balloon 14 and the inner tube 16 are then joined to each other (step of joining a balloon and an inner tube) as shown in FIGS. 8A and 8B. The inner tube 16 is first inserted into the interior of the balloon 14 and the shaft 12 as illustrated in FIG. 8A. The distal portion of the balloon 14 and the inner tube 16 are then fused to be joined to each other as shown in FIG. 8B.

Subsequently, a step of joining the distal tip 18 and the inner tube 16 to each other (step of joining a distal tip and an inner tube) is executed as shown in FIGS. 9A and 9B. First, the distal portion of the inner tube 16 is cut, thereby adjusting the length as shown in FIG. 9A. The proximal portion of the distal tip 18 is fitted to the distal portion of the inner tube 16 from the outside, and the proximal portion of the distal tip 18 and the distal portion of the inner tube 16 are fused to be joined to each other as illustrated in FIG. 9B.

Note that, joining the proximal end of the shaft 12 and the distal portion of the hub 20 to each other (step of joining a shaft and a hub) can be executed at an arbitrary time. For example, the step of joining a shaft and a hub may be executed before the step of joining the balloon 14 and the shaft 12, may be executed after the step of joining the distal tip 18 and the inner tube 16, or may be executed between the step of joining the balloon 14 and the shaft 12 and the step of joining the distal tip 18 and the inner tube 16.

In the above-described manufacturing method, fusing is described as an example for a method of joining members to one another. However, other types of joint means such as bonding may instead be applied.

The catheter 10 according to the present embodiment is basically configured as described above. Operations and effects of the catheter 10 will now be described.

An example of performing treatment using the catheter 10 is as follows. First, a lesion (stenosed portion) occurring inside a blood vessel is specified (identified) through an intravascular contrast method or an intravascular ultrasound diagnosis method. A guide wire 21 is percutaneously guided into the blood vessel in advance through, for example, a Seldinger's method. The guide wire 21 is then inserted through the wire lumen 16a of the inner tube 16 from the distal end opening portion 18a of the distal tip 18. While the guide wire 21 is guided out through the opening portion 22, the catheter 10 is inserted into the blood vessel. Under a radioscopic condition, the guide wire 21 is caused to advance toward the target lesion. The guide wire 21 is moved to pass through the lesion and to indwell, and the catheter 10 is moved to advance along the guide wire 21.

When the distal tip 18 of the catheter 10 passes through the lesion, the balloon 14 is positioned at the lesion. Inflation fluid (for example, contrast agent) is then pressure-fed into the inflation lumen 12*a* from the hub 20 side to inflate the balloon 14 and widen the lesion. Accordingly, treatment of the lesion can be performed. Subsequently, the dilation fluid is suctioned from the inside of the balloon 14 to the hub 20 side through the inflation lumen 12*a*, and the balloon 14 is deflated again. When an additional lesion required to be treated is present at a different part inside a body lumen, the balloon 14 is delivered (maneuvered) to the additional lesion and inflated and deflated in a similar manner as described above to widen the additional lesion. When the procedure for all of the lesions in a treatment object is completed, the catheter 10 is removed from the body.

As described above, high-pressure resistance and low compliance properties can be suitably applied to the balloon 14 because the reinforcement member 28 having the first threads 29 formed of the high-strength fibers is positioned radially between the inner layer 24 and the outer layer 26 of the balloon 14. Favorable flexibility of the balloon 14 can also be maintained because the reinforcement member 28 has a degree of freedom for moving relative to the balloon 14. Accordingly, it is possible to realize the balloon 14 having high crossability even inside a complicatedly meandering body lumen.

In the reinforcement member 28 of the embodiment described here, the intermediate portion 34 and at least one of the first end portion 31 or the second end portion 32 of the reinforcement member 28 are not directly fixed to the balloon 14. In other words, substantially the entirety of the reinforcement member 28 has the degree of freedom for moving in the axial direction and the circumferential direction relative to the balloon 14. Therefore, favorable flexibility of the balloon 14 can be maintained. The balloon 14 thus possesses high crossability inside a body lumen.

In the embodiment illustrated in FIG. 2, not only one of the first end portion 31 or the second end portion 32, but also the other end portion 31, 32, is not directly fixed to any one of the inner layer 24 and the outer layer 26. The reinforcement member 28 is thus not fixed to any portion of the balloon 14. Therefore, the degree of freedom for moving the reinforcement member 28 relative to the balloon 14 can be further improved, and flexibility can be improved. Crossability inside a body lumen can thus be further improved.

Figure 10:
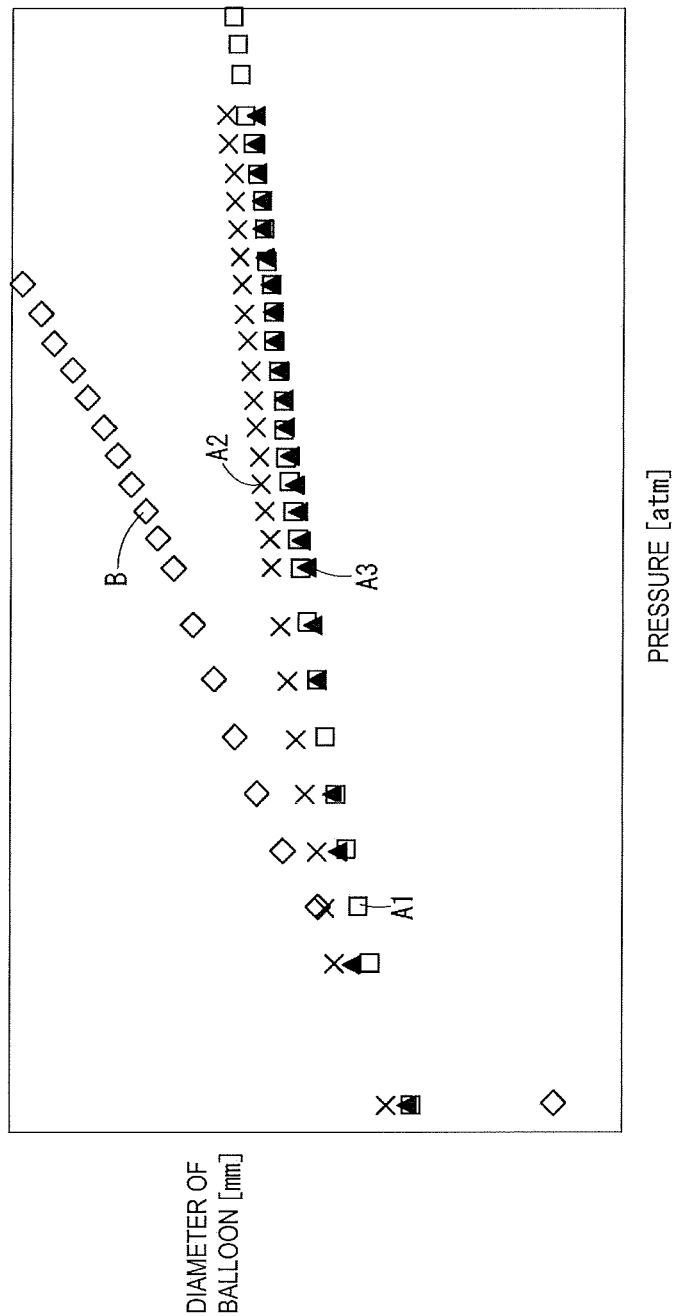
FIG. 10 is a graph illustrating the relationship between pressure and balloon outer diameter regarding balloons having forms of fixing the reinforcement member which are different from each other, and a balloon without a reinforcement member.

Here, FIG. 10 is a graph illustrating the relationship between pressure and balloon outer diameter regarding balloons A1 to A3. Balloons A1 to A3 are provided with the reinforcement member 28, but have different forms of fixing the reinforcement member 28. Balloon B is not provided with a reinforcement member 28. The balloon A1 has both end portions of the reinforcement member 28 in the axial direction fixed to the inner layer 24, the balloon A2 has only one end portion of the reinforcement member 28 in the axial direction fixed to the inner layer 24, and the balloon A3 has a reinforcement member 28 that is not fixed to any part of the inner layer 24.

As illustrated in FIG. 10, the balloons A1 to A3 provided with the reinforcement member 28, compared to the balloon B provided without a reinforcement member 28, have gentle (i.e., relatively smaller increases of balloon outer diameters relative to increases in internal pressure. Balloons A1 to A3 possess high pressure resistance and low compliance properties relative to balloon B that does not include the reinforcement member 28. Meanwhile, no meaningful (significant) difference based on the type of fixing the reinforcement member 28 is recognized in the balloons A1 to A3 that are provided with the reinforcement member 28. Therefore, it is understood that a balloon having high-pressure resistance and low compliance properties can be realized by providing the reinforcement member 28 between the inner layer 24 and the outer layer 26, regardless of whether the reinforcement member 28 is fixed. From the viewpoint of maintaining favorable flexibility of the balloon 14 and improving crossability of the catheter 10 inside a body lumen, it is thus favorable that the intermediate portion 34 and at least one the end portions of the reinforcement member 28 are not fixed to the inner layer 24 and the outer layer 26 of the balloon 14.

When the balloon 14 of the catheter 10 is inflated, the inflation restriction portions 36 restrict inflation of both the end portions of the reinforcement member 28 in the axial direction. Therefore, the balloon 14 can be inflated to have a desired shape inside a body lumen, and a procedure can be effectively performed with respect to a lesion. The inflation restriction portion 36 is formed of a fusible material and is fused to the first thread 29, and so the reinforcement member 28 in which inflation of both the end portions are restricted can be conveniently manufactured.

The catheter 10 includes the tubularly net-shaped body 37 conducting a pressure-resistant function. The tubularly net-shaped body 37 is configured with the first thread 29 formed of a high-strength fiber. The second thread 30 conducts a fusing function independent of the tubularly net-shaped body 37 and is disposed along the tubularly net-shaped body 37. Therefore, a portion conducting the pressure-resistant function and a portion conducting the fusing function are independently established from each other. Accordingly, the pressure-resistant function and the fusing function can be individually set. Thus, the reinforcement member 28 which has desired pressure resistance and in which inflation of both the end portions is restricted can be simply established.

In addition, the balloon 14 of the present embodiment is inflated and deflated while entailing elastic stretching and is a zero folding-type balloon (which is not folded when being in a deflated state). Accordingly, the balloon can easily restore the original outer diameter when the balloon is deflated. When multiple lesions occur in different locations inside a body lumen, the same balloon 14 can be used to treat the multiple lesions because the outer diameter of the balloon 14 after being deflated does not become greater than the initial outer diameter of the balloon 14. Therefore, even after the balloon 14 is deflated again, favorable crossability (maneuverability) inside a body lumen can be maintained.

The balloon 14 having elastic stretching properties (i.e., a relatively elastic balloon 14) can be prepared without performing blow molding. Therefore, the catheter 10 can be conveniently manufactured. In other words, when a balloon is configured with a non-stretchable material, the balloon is required to be molded to have a desired shape by executing blow molding after manufacturing the base material of the balloon. Moreover, there is a need to execute a wrapping step in which the balloon is folded (one or more outer circumferential portions of the balloon are folded in the circumferential direction in an overlapping manner) to put the balloon in a deflated state. In contrast, the balloon 14 of the present embodiment does not require blow molding and does not require the wrapping step during manufacturing. Therefore, it is possible to reduce the number of manufacturing steps and to lower the manufacturing cost.

In addition, inflation in the circumferential direction and the radial direction is restricted by the inflation restriction portion 36 (refer to FIG. 2) at the first end portion 31 and the second end portion 32 of the reinforcement member 28.

According to this configuration, the maximally inflated diameter of the intermediate portion 34 of the reinforcement member 28 positioned between the first end portion 31 and the second end portion 32 can be effectively restricted. Therefore, the function as the reinforcement member 28 can be suitably conducted.

As described above, the reinforcement member 28 may be formed by tubularly knitting one or more first threads 29, and the waved first threads 29 adjacent to each other in the axial direction are interlaced with each other (refer to FIG. 3A). When the reinforcement member 28 is compressed in the circumferential direction, the first threads 29 become folded in the circumferential direction. When the reinforcement member 28 is compressed in the axial direction, the first threads 29 of the meshes become misaligned in the axial direction. Therefore, the reinforcement member 28 in this configuration can be flexibly bent.

In the reinforcement member 28 in which the meandering (i.e., wavy or bent) first threads 29 adjacent to each other in the axial direction are interlaced with each other, the interlaced portion of the first threads 29 configures an interlock portion. In the interlock portion, the first threads 29 are not bonded to each other. The first threads 29 are formed to be movable relative to each other. According to this configuration, the reinforcement member 28 can be bent in accordance with rotations of the interlaced portion of the first threads 29. Therefore, flexibility of the balloon 14 can be further enhanced.

The base material sleeve 50 in the catheter manufacturing method described above is heated and cut. Therefore, when the reinforcement member 28 is cut from the base material sleeve 50 to a desired length, a fusible material is fused at the heated portion to form the ring-shaped inflation restriction portion 36 fused to the first thread 29. In contrast, when a reinforcement member (not illustrated) only includes the first thread 29 (high-strength fiber), the high-strength fiber is not generally fused and there is little (extremely low) fusing properties. Therefore, fibers are unlikely to be fused to each other at both the end portions of the reinforcement member, and both the end portions are not restricted from moving in the circumferential and radial directions during inflation/deflation of the balloon. The reinforcement member 28 (in which inflation of both the end portions is restricted) of the catheter 10 disclosed here can thus be conveniently manufactured.

When the outer sides of the multiple second threads 30 disposed along the outer surface of the mandrel 39 are covered with the tubularly net-shaped body 37, the multiple second wire-shaped members are held between the tubularly net-shaped body 37 and the mandrel 39. Thus, the reinforcement member 28 can be efficiently prepared.

Figure 11:
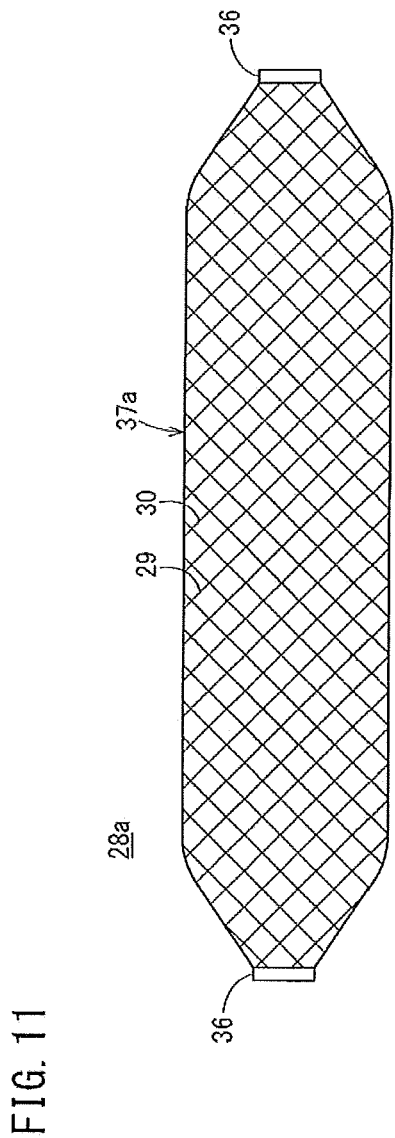
FIG. 11 is a side view when the reinforcement member according to a modification example is inflated.

In the catheter 10 described above, a reinforcement member 28a illustrated in FIG. 11 may be applied instead of the reinforcement member 28 illustrated in FIG. 2. In the reinforcement member 28a, one or more first threads 29 formed of high-strength fibers, and one or more second threads 30 formed of fusible materials, collectively form a tubularly net-shaped body 37a. The method of forming the tubularly net-shaped body 37a is not particularly limited, and the method can be performed through tube-knitting, braiding, and the like as described above.

The first thread 29 and the second thread 30 are knitted together to form the tubularly net-shaped body 37a. Therefore, in the base material sleeve preparation step regarding the manufacture of the reinforcement member 28a, a base material sleeve is prepared by knitting the first thread 29 and the second thread 30, and then one or more spots of the base material sleeve in the axial direction are heated and cut. Accordingly, the reinforcement member 28a in which the inflation restriction portions 36 are formed at both the end portions can be simply manufactured.

Pressure resistance required in the reinforcement member 28a can be suitably ensured when the cross-sectional area of the cross-section perpendicular to the axial direction of the reinforcement member 28a in the first thread 29 is greater than the cross-sectional area of that in the second thread 30. In this case, the base material sleeve is formed such that the cross-sectional area of the cross-section perpendicular to the axial direction of the base material sleeve in the first thread 29 is greater than the cross-sectional area of that in the second thread 30.

For example, the cross-sectional area in the first thread 29 may be greater than the cross-sectional area in the second thread 30 by increasing the number of the first threads 29 configuring the base material sleeve to exceed the number of the second threads 30, or by increasing the thickness of the first thread 29 configuring the base material sleeve to exceed the thickness of the second thread 30. Alternatively, the cross-sectional area in the first thread 29 may be greater than the cross-sectional area in the second thread 30 by adjusting the number and the thickness of the first threads 29 and the second threads 30.

The detailed description above describes a catheter and a catheter manufacturing method. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A catheter comprising: a balloon comprising an elastic inner layer and an elastic outer layer, the inner layer and the outer layer being tubularly shaped and extending in an axial direction, the inner layer and the outer layer being inflatable and deflatable in a radial direction in response to a change of internal pressure of the balloon;
   a tubular reinforcement member positioned between the inner layer and the outer layer in the radial direction, at least part of the reinforcement member being not directly fixed to the inner layer and the outer layer,
   the reinforcement member comprising a first wire-shaped member formed of a high-strength fiber, the reinforcement member possessing a first end portion and a second end portion opposite the first end portion in the axial direction; and
   the first end portion and the second end portion of the reinforcement member each include a ring-shaped inflation restrictor fused to the first wire-shaped member, the inflation restrictors restricting inflation of both the first end portion and the second end portion of the reinforcement member in the radial direction when the inner layer and the outer layer inflate in the radial direction in response to the change of the internal pressure of the balloon.

2. The catheter according to claim 1, wherein
   the reinforcement member comprises a second wire-shaped member comprising a fusible material, and
   the second wire-shaped member is the same material as the ring-shaped inflation restrictors.

3. The catheter according to claim 2, wherein
   the first wire-shaped member forms a tubularly net-shaped body, the tubularly net-shaped body extending in the axial direction and possessing a circumferential direction, the tubularly net-shaped body possessing one end portion and an other end portion opposite the one end portion in the axial direction, the second wire-shaped member of the reinforcement member is one of a plurality of second wire-shaped members, each of the plurality of second wire-shaped members comprising the fusible material, and the plurality of second wire-shaped members are spaced apart from one another in the circumferential direction of the tubularly net-shaped body, the plurality of second wire-shaped members each extending in the axial direction along the tubularly net-shaped body from the one end portion to the other end portion of the tubularly net-shaped body, the plurality of second wire-shaped members each being interlocked with the inflation restrictors at both of the first and second end portions of the reinforcement member.

4. The catheter according to claim 2, wherein the first wire-shaped member and the second wire-shaped member together form a tubularly net-shaped body.

5. The catheter according to claim 4, wherein a cross-sectional area of a cross section perpendicular to the axial direction of the first wire-shaped member is greater than a cross-sectional area perpendicular to the axial direction of the second wire-shaped member.

6. A catheter comprising:
an elongated shaft extending in an axial direction;
a balloon connected to the elongated shaft, the balloon comprising an elastic inner layer and an elastic outer layer, the inner layer and the outer layer being tubularly shaped and extending in the axial direction, the inner layer and the outer layer being inflatable and deflatable in a radial direction in response to a change of internal pressure of the balloon;
a tubular reinforcement member positioned between the inner layer and the outer layer of the balloon in the radial direction, at least part of the reinforcement member being movable relative to the inner layer and the outer layer,
the reinforcement member comprising a first wire-shaped member, the reinforcement member possessing a first end portion and a second end portion opposite the first end portion in the axial direction;
both the first end portion and the second end portion of the reinforcement member including ring-shaped inflation restrictors fused to the first wire-shaped member, the inflation restrictors restricting inflation of both the first end portion and the second end portion of the reinforcement member in the radial direction when the inner layer and the outer layer inflate in the radial direction in response to the change of the internal pressure of the balloon; and the reinforcement member being configured to restrict inflation of the inner layer and the outer layer of the balloon so that the balloon possesses a cylindrically-shaped outer diameter intermediate portion when the balloon is fully inflated.

7. The catheter according to claim 6, wherein the reinforcement member comprises a second wire-shaped member comprising a fusible material.

8. The catheter according to claim 7, wherein the ring-shaped inflation restrictors are the same material as the second-wire shaped member.

9. The catheter according to claim 8, wherein
the first wire-shaped member forms a tubularly net-shaped body, the tubularly net-shaped body extending in the axial direction and possessing a circumferential direction, the tubularly net-shaped body possessing one end portion and an other end portion opposite the one end portion in the axial direction, the second wire-shaped member of the reinforcement member is one of a plurality of second wire-shaped members, each of the plurality of second wire-shaped members comprising the fusible material, and the plurality of second wire-shaped members are spaced apart from one another in the circumferential direction of the tubularly net-shaped body, the plurality of second wire-shaped members each extending in the axial direction along the tubularly net-shaped body from the one end portion to the other end portion of the tubularly net-shaped body, the plurality of second wire-shaped members each being interlocked with the inflation restrictors at both of the first and second end portions of the reinforcement member.

10. The catheter according to claim 7, wherein the first wire-shaped member and the second wire-shaped member together form a tubularly net-shaped body.

11. The catheter according to claim 10, wherein
the first wire-shaped member extends in the axial direction and the second wire-shaped member extends in the axial direction, and a cross-sectional area of a cross section perpendicular to the axial direction of the first wire-shaped member is greater than a cross-sectional area perpendicular to the axial direction of the second wire-shaped member.

12. The catheter according to claim 7, wherein at least a portion of the first wire-shaped member is not bonded to at least a portion of the second wire-shaped member.

* * * * *